(12) United States Patent
Becker

(10) Patent No.: US 6,483,000 B2
(45) Date of Patent: Nov. 19, 2002

(54) PROCESS FOR THE MANUFACTURE IN PURE FORM OF 1-PENTENE OR AN ALPHA-OLEFIN LOWER THAN 1-PENTENE

(75) Inventor: Hans Becker, Munich (DE)

(73) Assignee: Sasol Technology (Pty) LTD, Johannesburg (ZA)

( * ) Notice: Subject to any disclaimer, the term of this patent is extended or adjusted under 35 U.S.C. 154(b) by 0 days.

(21) Appl. No.: 09/848,558

(22) Filed: May 3, 2001

(65) Prior Publication Data

US 2002/0004534 A1 Jan. 10, 2002

(30) Foreign Application Priority Data

May 9, 2000 (DE) .......................... 100 22 467

(51) Int. Cl.[7] .......................... C07C 41/00; C07C 9/00; C07C 2/00; C07C 7/00
(52) U.S. Cl. .................. 585/800; 585/802; 585/807; 585/809; 585/820; 585/833; 585/500
(58) Field of Search .................. 585/800, 802, 585/807, 809, 820, 833, 500

(56) References Cited

U.S. PATENT DOCUMENTS 5,994,594 A * 11/1999 Marion et al. .............. 568/579

FOREIGN PATENT DOCUMENTS

DE 19723049 6/1997
DE 19825295 6/1998

OTHER PUBLICATIONS

Render, C., et al.; "Sasol Alpha Olefins"; (lecture material used for the lecture at ACHEMA 94).

* cited by examiner

Primary Examiner—Walter D. Griffin
Assistant Examiner—Tam N. Nguyen
(74) Attorney, Agent, or Firm—Knobbe, Martens, Olson & Bear, LLP

(57) ABSTRACT

The invention relates to a process for the recovery as a feedstock of an alpha-olefin from a mixture containing mainly hydrocarbon compounds, such as is obtained by Fischer-Tropsch-synthesis after an at least crude separation of components boiling higher and/or lower than the alpha-olefin, wherein tertiary olefins of the mixture, after superstoichiometrical addition of a low alcohol, are subjected to catalytic etherification and a stream derived by etherification is fed jointly with the alpha-olefin and the ethers produced and other high boiling reaction products to a distillative separation of components boiling higher than the olefin.

16 Claims, 3 Drawing Sheets

US 6,483,000 B2

PROCESS FOR THE MANUFACTURE IN PURE FORM OF 1-PENTENE OR AN ALPHA-OLEFIN LOWER THAN 1-PENTENE

FIELD OF THE INVENTION

The invention relates to a process for the recovery as a feedstock of an alpha-olefin from a mixture containing mainly hydrocarbon compounds.

BACKGROUND TO THE INVENTION

In a published concise rendition of a lecture: C L Render, Z Denga "Sasol Alpha Olefins" from the lecture series "New processes in chemical technology" at the ACHEMA Congress 1994, a process is described which permits the recovery of alpha-olefins and more particularly 1-pentene and 1-hexene in relatively pure form from the liquid fraction produced in the Fischer-Tropsch-Synthesis. Since a large number of other compounds of various types boil in the immediate vicinity of the boiling temperature of the desired alpha-olefins, of which some even form azeotropic mixtures with the desired alpha-olefins, and although the distillative separation of interfering contaminants represents an important process step, it is nevertheless not possible with acceptable effort to attain the desired purity of the alpha-olefin product solely by distillation.

Accordingly, tertiary olefins are first converted with methanol into ethers in a pentene or hexene fraction preconcentrated by distillation. This etherification step is followed in a so-called superfractionation by a sharp distillative separation of all the components which are either lower or higher boiling than the desired alpha-olefin. Jointly with the lower boiling components excess methanol derived from the etherification step is also separated. From this low boiling fraction the methanol is extracted with water and is recovered from the aqueous extract by a distillative methanol/water separation.

Jointly with the higher boiling components the ethers formed in the etherification step are likewise separated.

The alpha-olefin crude product of superfractionation has a typical purity of about 90%. It now only contains components which boil very close to the desired alpha-olefin and which, therefore, can be separated by normal distillation only with extremely great efforts. However, all these interfering components differ from desired alpha-olefins by their polarity and may, therefore, be separated relatively easily in the polar medium of the extractive distillation succeeding the superfractionation. The extractive distillation is performed with aqueous NMP (N-methyl-2-pyrrolidon) as a solvent. Accordingly, the alpha-olefin final product must still be dried. This is done by a distillative separation of the water.

An improvement of this known process for the recovery of alpha-olefins was filed as a patent application at the German Patent Office under file number 197 23 049. An important integer of this improved process resides in the provision of the etherification reactor downstream of the distillative fine separation of all lower boiling components (lower boiling than the desired alpha-olefin).

Due to a reaction equilibrium arising in the etherification reactor, it is not possible to attain a complete conversion of the tertiary olefins into the corresponding ethers. Depending on the original content of tertiary olefins there accordingly arises a maximum attainable purity of the alpha-olefin product, hardly exceeding 99%—even after practically complete removal of all other impurities. (Here and in what follows the purity is stated in percentages by mass). This applies to the process according to C L Render and Z Denga as well as to the improved process (197 23 049.0).

The process described by C L Render and Z Denga is well suited to recover from the fractions obtained in the coal liquefaction according to Fischer-Tropsch, e.g. 1-hexene with a purity of 98.5%. Higher purities can only be attained with progressively increasing yield losses. The reason therefor resides in the tertiary olefins accompanying the feedstock and the boiling points of which are close to 1-hexene and which, therefore, can virtually not be separated off by conventional separating methods. These tertiary olefins must be converted in the reactor to separable compounds. In a singe-stage reactor the degree of conversion is limited, however, by the chemical equilibrium so that the maximum attainable purity of the 1-hexene product is ultimately limited by the reaction equilibrium.

In order to overcome this limitation regarding attainable purity to about 99% a process is proposed in DE 198 25 295 A1.

From a mixture containing predominantly hydrocarbon compounds, as obtained in Fischer-Tropsch-Synthesis, alpha-olefins are recovered after an at least crude separation of components boiling higher and/or lower than the alpha-olefin. For that purpose tertiary olefins of the mixture boiling close to the alpha-olefin to be recovered are subjected to a catalytic etherification after a superstoichiometric addition of a low alcohol. A stream of ethers and other high boiling reaction products recovered from the etherification together with the alpha-olefin is forwarded to a distillative separation of components boiling higher than the olefin.

The etherification is performed in multiple stages, at least in two stages. After each etherification step etherification products are separated as residue streams, where applicable jointly with other higher boiling components.

In addition, it is proposed to separate the low boiling alcohol as an azeotropic mixture after the etherification and separation of the etherification products in a further distillation step and to subject the olefin fraction so obtained when desired or required to further separation steps, e.g. an extractive distillation and/or an adsorption.

The process disclosed in DE 198 25 295 A1 is directed at recovering by the same method a variety of alpha-olefins, in particular, however, 1-hexene or alternatively 1-pentene having a purity in excess of 99%.

Although the problems of purifying e.g. 1-hexene or 1-pentene are similar, they are not identical. Accordingly, the process according to the state of the art is not equally suitable for the recover of whatever alpha-olefin.

Accordingly, a need exists for a more simple process than that in the prior art for the recovery of 1-pentene and alpha-olefins boiling lower than 1-pentene.

SUMMARY OF THE INVENTION

The invention provides a process for the recovery as a feedstock of an alpha-olefin from a mixture containing mainly hydrocarbon compounds, such as is obtained by Fischer-Tropsch-synthesis after an at least crude separation of components boiling higher and/or lower than the alpha-olefin, wherein tertiary olefins of the mixture, after superstoichiometrical addition of a low alcohol, are subjected to catalytic etherification and a stream derived by etherification is fed jointly with the alpha-olefin and the ethers produced and other high boiling reaction products to a distillative separation of components boiling higher than the olefin.

Thus, according to a first aspect of the invention, there is provided a process for the recovery as a feedstock of an alpha-olefin from a mixture containing mainly hydrocarbon compounds, such as is obtained by Fischer-Tropsch-synthesis after an at least crude separation of components boiling higher and/or lower than the alpha-olefin, wherein tertiary olefins of the mixture, after super-stoichiometrical addition of a low alcohol, are subjected to catalytic etherification and a stream derived by etherification is fed jointly with the alpha-olefin and the ethers produced and other high boiling reaction products to a distillative separation of components boiling higher than the olefin, in which from the mixture, 1-pentene or an alpha-olefin lower boiling than 1-pentene is recovered, wherein after a distillative fine separation of substances lower boiling than the alpha-olefin to be recovered from the mixture the etherification is performed with excess methanol in a single or a plurality of stages;

during the distillative separation of the components higher boiling than the alpha-olefin from the stream derived by the etherification a by-product is separated, comprising ethers and other components higher boiling than the alpha-olefin and a stream comprising the alpha-olefin and the excess methanol is recovered and subjected to an extractive distillation with methanol as solvent; and the excess methanol is recovered approximately completely during the extractive distillation and is returned to the etherification stage, supplemented by a methanol feed stream.

By the limitation to the recovery of 1-pentene or an alpha-olefin boiling lower than 1-pentene and to mixtures, in which prior to the etherification the components boiling lower than the alpha-olefin are separated by fine separation, a low throughput in the process steps downstream of the fine separation is attained and a simplified overall process including less separation effort.

As a result of the excess methanol from the etherification being reused in the extractive distillation performed downstream, it is possible to perform the etherification with a virtually unlimited methanol excess. This results in a more complete etherification than in the process according to the state of the art. As a result it is in many cases possible to dispense with a second etherification step. The reactor required for the etherification may, due to the fine separation performed upstream and the more effective etherification, be restricted to small dimensions.

Due to the fact that in the etherification methanol is employed as a reactant and downstream methanol is also used as a solvent in the extractive distillation, a separate infrastructure for the provision of a solvent for the extraction, as is required in the process according to DE 198 25 295 A1, can be dispensed with.

The recovery of the excess methanol in the course of the processing of the solvent for the extractive distillation which is necessary in any case and the reuse of the methanol during the etherification jointly with an added methanol feed stream, reduces the amount of methanol to be employed to just little more than the amount which is used during the etherification.

In an embodiment of the process according to the invention the stream including the olefin and the excess methanol are fed into an absorber of the extractive distillation in order to separate oxygenates and dienes, wherein methanol is used as a solvent and the remaining gaseous olefin stream is subjected to scrubbing with water in order to remove methanol.

The scrubbed olefin stream may be subjected to a distillative drying step.

In order to be dried, the scrubbed olefin stream may be cooled, olefins and water be condensed, be separated by decanting, the water fraction be fed into the water scrubbing stage for methanol removal and dissolved water may be extracted from the liquid olefin fraction by means of a heated drying column and a dry olefin production stream may be recovered.

Firstly, a liquid methanol stream including the oxygenates, dienes and a little olefin derived from the heated sump of the absorber and secondly a methanol/water mixture virtually free of oxygenate and diene derived from the lower part of the water scrubbing stage of the olefin may be passed to a methanol stripper for purposes of regeneration.

By means of the methanol stripper it is possible to produce a sump product, comprising virtually methanol-free water, a virtually oxygenate-free and diene-free methanol stream including a little water may be withdrawn in a first side outlet and be used in the absorber as a solvent, and a virtually water-free methanol stream containing little oxygenate and diene may be withdrawn in a second side outlet and returned to the etherification.

In a section of the methanol stripper above the second side outlet oxygenates and dienes may be enriched in the rising gas and be passed by way of a chimney tray into a head portion of the methanol stripper, further methanol being scrubbed out in the head portion by means of water scrubbing, and a virtually methanol-free overhead gas be recovered jointly with the oxygenates and dienes and the scrubbing water with the methanol dissolved therein be forwarded to a lower section of the methanol stripper.

The virtually methanol-free overhead gas may be condensed, a water fraction and a fraction including the oxygenates and dienes being formed by decanting, the water fraction being used for water scrubbing in the head portion of the methanol stripper and the fraction including the oxygenates and dienes being fed partly below the chimney tray as a reflux liquid and partly being fed as a by-product stream to some further use.

The methanol-free water from the sump of the methanol stripper can be used in one portion in the water scrubbing in the head portion of the methanol stripper and in another portion in the water scrubbing of the olefin stream.

In an alternative embodiment of the process according to the invention, there is fed firstly from the heated sump of the absorber a liquid methanol stream including the oxygenates, dienes and a little alpha-olefin to a methanol regenerating column and secondly an almost oxygenate and diene-free methanol/water mixture from the lower part of the water scrubbing stage of the olefin to a methanol/water separating column.

By means of the methanol/water separating column it is possible to produce almost methanol-, oxygenate- and diene-free water as a sump product and, in addition, to withdraw an oxygenate- and diene-containing methanol overhead product, condensed and used in one portion as a solvent in the methanol/water separating column and in another portion be fed into the methanol regenerating column.

From the sump of the methanol regenerating column and almost oxygenate- and diene-free methanol stream may be withdrawn, one portion thereof being used in the absorber as a solvent and another portion being returned to the etherification step.

In the methanol regeneration column oxygenates and dienes may be enriched in the rising gases and be passed by way of a chimney tray into a head portion of the methanol regenerating column, further methanol being scrubbed out by water scrubbing in the head portion and a virtually methanol-free overhead gas being recovered with the oxygenates and dienes and the scrubbing water with the dissolved methanol being passed into the methanol/water separating column.

The virtually methanol-free overhead gas is advantageously condensed, by decantation a water fraction and a fraction containing the oxygenates and dienes are formed, the water fraction is used for water scrubbing in the overhead portion of the methanol regenerating column and the fraction comprising the oxygenates and dienes is in part fed below the chimney tray as reflux liquor and for another part is passed as a by-product stream to further use.

The methanol-free water from the sump of the methanol/water separating column may in part be used in the water scrubbing in the head portion of the methanol regenerating column and to another part in the water scrubbing of the olefin stream.

DESCRIPTION OF THE DRAWINGS

The invention will be further elucidated by way of example only, by the recovery of 1-pentene with reference to two embodiments and three figures. Equivalent parts in the figures are denoted by the same reference symbols.

In the drawings,

In FIG. 1 are illustrated the main process streams and the sequence of the process steps in accordance with the invention.

Figure 1:
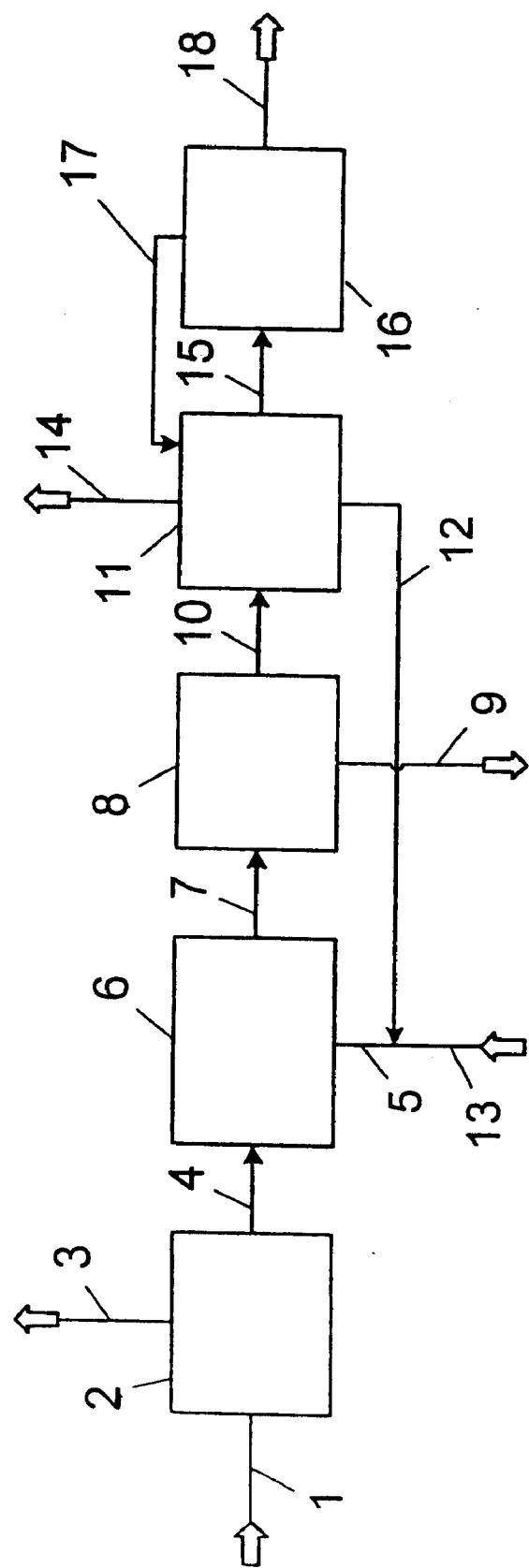
FIG. 1 represents a block diagram of a process according to the invention.

A fraction including the 1-pentene to be recovered and hydrocarbon compounds, of which those boiling lower and higher than the 1-pentene have been separated only crudely (not shown in FIG. 1) are employed as feed stream 1 and are subjected to a distillative fine separation 2.

In the fine separation 2 a first by-product stream 3 including substances boiling lower than the 1-pentene and a stream 4 including the 1-pentene are formed and are subjected with the addition of an excess of methanol 5 to an etherification 6.

In the etherification 6 tertiary olefins boiling close to 1-pentene are subjected to a catalytic etherification and a stream 7 including the 1-pentene and the etherification products is produced and subjected to a distillative fine separation 8 of the etherification products and other components boiling higher than 1-pentene. In doing so, a second by-product stream 9 including the etherification products is recovered. Furthermore, a stream 10 including the 1-pentene and the excess methanol is produced and subjected to an extractive distillation 11 using methanol as solvent.

In the course of a methanol regeneration and methanol/water separation (not illustrated in FIG. 1) the excess methanol is recovered almost completely in the course of the extractive distillation and returned to the etherification 6 as a methanol stream 12, replenished by a methanol feed stream 13. In addition, in the extractive distillation 11 a third by-product stream 14 including oxygenates and dienes is recovered and finally an aqueous 1-pentene crude product 15 derived from the extractive distillation 11 is subjected to a distillative drying step 16. A water fraction 17 separated thereby is used in the extractive distillation 11 for scrubbing out methanol and a product stream 18 including almost water-free 1-pentene is recovered. The by-product streams 3, 9, 14 and the product stream 18 are passed on to a use which is not illustrated in FIG. 1.

Figure 2:
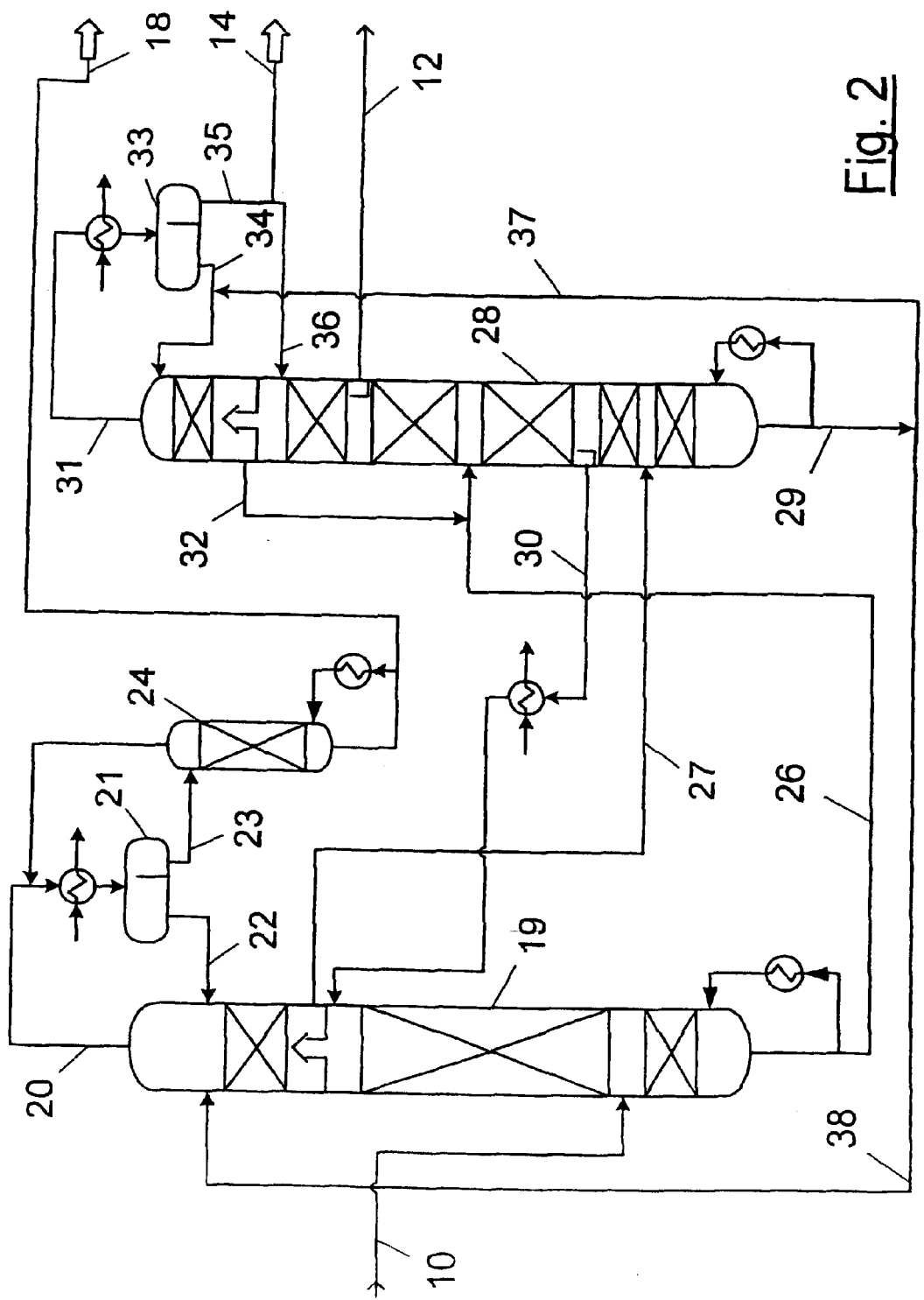
FIG. 2 represents an embodiment of the extractive distillation including a methanol regeneration and methanol/water separation, jointly with a single stripping column.

In FIG. 2 an embodiment of the extractive distillation and the recovery of the product stream including the 1-pentene is illustrated by way of a simplified flow diagram. Methanol regeneration required for the extractive distillation and methanol/water separation are performed jointly in a single stripping column.

The stream 10 including the 1-pentene and the excess methanol is passed for separating the oxygenates and dienes into the lower part of the absorber 19 of the extractive distillation in which methanol is used as a solvent. The remaining gaseous 1-pentene stream is subjected to water scrubbing in a portion of the absorber 19, separated by a chimney tray.

A scrubbed 1-pentene stream 20 from the upper portion of the absorber 19 is subjected to a distillative drying step. For this purpose the scrubbed 1-pentene stream 20 is cooled, olefin and water are condensed and separated by decanting 21. A water fraction 22 obtained by decantation is fed into the upper portion of the absorber 19 as a scrubbing medium and a liquid 1-pentene fraction 23 formed during the decantation 21 has dissolved water extracted therefrom by means of a heated drying column 24, whereby a dry product stream 18 including the 1-pentene is recovered and passed on to a use not illustrated in FIG. 2.

From the heated sump of the lower part of the absorber 19 a liquid methanol stream 26 loaded with the oxygenates and dienes is withdrawn. At the upper part of the absorber 19 a virtually oxygenate- and diene-free methanol/water mixture 27 is withdrawn in a side outlet. The methanol stream 26 and the methanol/water mixture 27 are each passed to regeneration at a suitable feed locality of a methanol stripper 28. By means of the methanol stripper 28 a virtually methanol-free water is produced as a sump product 29. In a first side outlet of the methanol stripper 28 a virtually oxygenate- and diene-free stream 30 containing only little water is withdrawn and used as a solvent in a lower part of the absorber 19. In a second side outlet of the methanol stripper a virtually water-free methanol stream 12 containing only little oxygenates and dienes is withdrawn and returned to the etherification stage 6 (in FIG. 1). In a section of the methanol stripper 28 above the second side outlet oxygenates and dienes are enriched in the rising gases and passed by way of a chimney tray into a head portion of the methanol stripper 28. There further methanol is scrubbed out by means of a water scrubbing stage and an overhead gas 31 virtually free of methanol including the oxygenates and dienes is formed and the scrubbing water 32, containing dissolved methanol is passed into a lower section of the methanol stripper 28.

The virtually methanol-free overhead gas 31 of the methanol stripper 28 is condensed and a water fraction 34 and a fraction 35 including the oxygenates and dienes are formed by decantation 33. The water fraction 34 is used for the water scrubbing in the head portion of the methanol stripper 28. The fraction 35 including the oxygenates and dienes is passed in part below the chimney tray as a reflux liquor 36 and for another part is recovered as the third by-product stream 14 and further utilised. The sump product 29 from the methanol stripper 28 including the virtually methanol-free water is used in one part 37 for the water scrubbing in the head portion of the methanol stripper 28 and for another portion 38 for the water scrubbing in the upper portion of the absorber 19.

Figure 3:
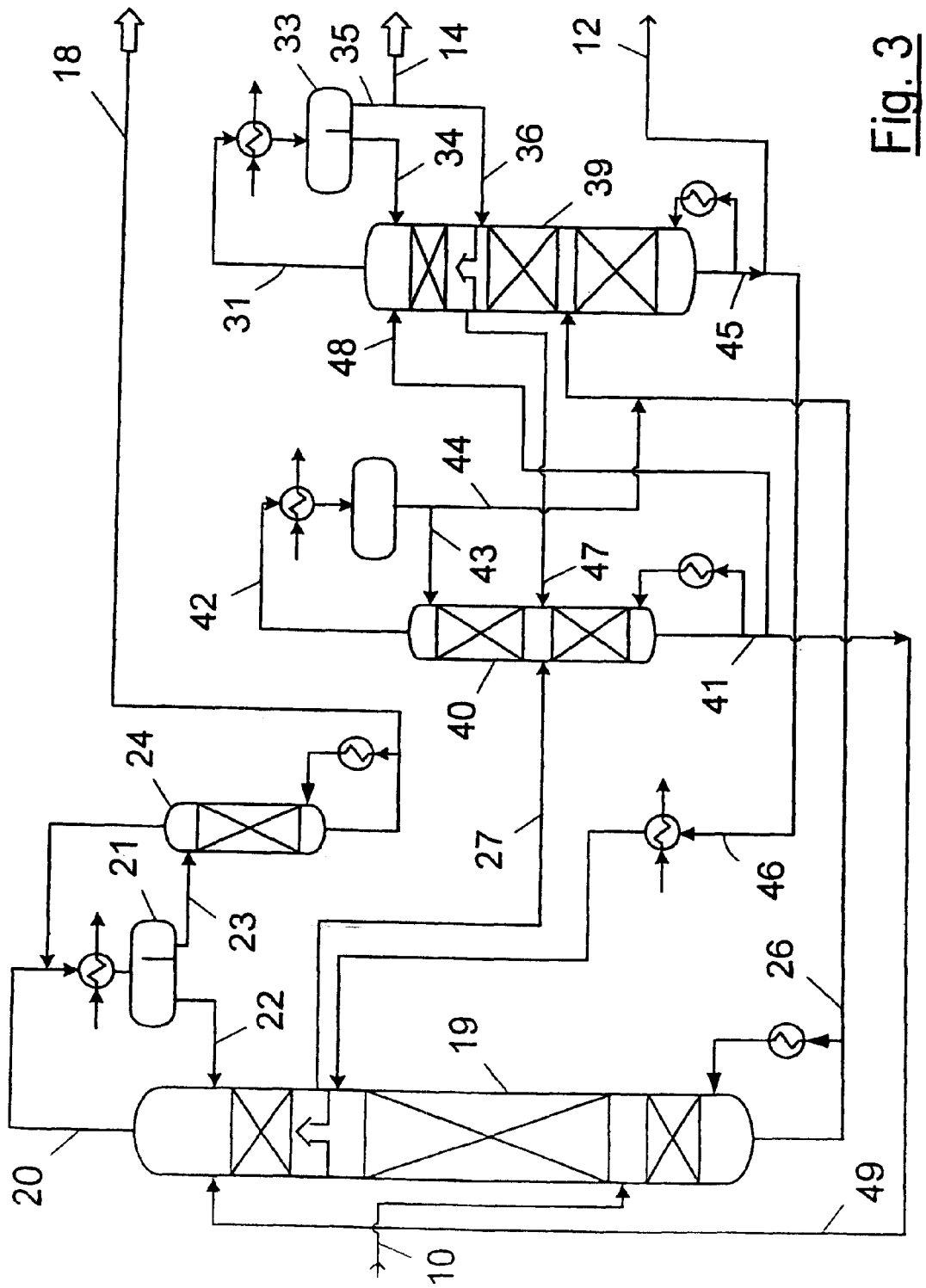
FIG. 3 represents an extractive distillation including methanol regeneration and methanol/water separation in separate columns.

In FIG. 3, by way of a simplified flow diagram, a further embodiment of the extractive distillation and the recovery of the product stream including the 1-pentene is illustrated. A methanol regeneration required for the extractive distillation and methanol/water separation are each performed in separate columns as an alternative to what is shown in FIG. 2.

As distinct from the embodiment according to FIG. 2, there is firstly fed into a methanol regenerating column 39 the liquid methanol stream 26 including the oxygenates and dienes and a little 1-pentene from the heated sump of the lower part of the absorber 19. Secondly, the virtually oxygenate- and diene-free methanol/water mixture 27 from the upper portion of the absorber 19 is passed into a methanol/water separating column 40. By means of the methanol/water separation virtually methanol-free water is formed as a sump product 41 and in addition an oxygenate- and diene-containing methanol overhead product 42 is withdrawn, condensed and in one portion 43 is fed as reflux into the methanol/water separating column 40 and in another portion 44 is passed to the methanol regenerating column 39. A virtually oxygenate- and diene-free methanol stream 45 is withdrawn from the sump of the methanol regenerating column 39 and in one portion 46 thereof used as solvent in the absorber 19 and in another portion returned as methanol stream 12 to the etherification 6 (FIG. 1).

In the methanol regeneration column 39 oxygenates and dienes are enriched in the rising gas and passed by way of a chimney tray in a head portion of the methanol regenerating column 39. In the head portion further methanol is scrubbed out by means of water scrubbing and a virtually methanol-free overhead gas 31 including the oxygenates and dienes is recovered and the scrubbing water 47 including the dissolved methanol is fed into the methanol/water separating column 40. The virtually methanol-free overhead gas 31 is condensed, a water fraction 34 is formed by decantation as well a fraction 35 including the oxygenates and dienes.

The water fraction 34 is used for water scrubbing in the head portion of the methanol regenerating column 39. The fraction including the oxygenates and dienes 35 is fed in one portion below the chimney tray of the methanol regenerating column 39 serving as reflux liquor and in another portion as a by-product stream 14 passed to further use.

The methanol-free water 41 from the sump of the methanol/water separating column 40 is used in one portion 47 in the water scrubbing stage in the head portion of the methanol regenerating column 39 and in another portion 49 in the water scrubbing in the upper part of the absorber 19.

The recovery of the product stream 18 including the 1-pentene takes place from the scrubbed 1-pentene stream 20 as described above with reference to FIG. 2.

German Patent Application DE 100 22 467.9 from which this application claims priority is incorporated herein by reference and forms and integral part of the disclosure.

The claims that follow form an integral part of the disclosure of the specification.

What is claimed is:

1. A process for the recovery of an alpha-olefin from a mixture comprising mainly hydrocarbon compounds, wherein the mixture is a product of a Fischer-Tropsch synthesis, wherein the product is subjected to at least one crude separation of at least one component having a higher boiling point than the alpha-olefin or at least one component having a lower boiling point than the alpha-olefin, the mixture comprising at least one tertiary olefin, said process comprising:

distilling the mixture to separate at least one component having a boiling point lower than the alpha-olefin, thereby forming a high-boiling mixture;

conducting an etherification wherein said high-boiling mixture is contacted with methanol present in a super-stoichiometric amount in the presence of a catalyst in at least one stage, whereby the tertiary olefin in said high-boiling mixture is reacted with methanol to form at least one ether, thereby forming an etherification mixture;

distilling the etherification mixture to separate at least one component having a boiling point higher than the alpha-olefin, thereby forming a product stream, the product stream comprising the alpha-olefin and methanol, the product stream having a boiling point below the boiling point of the component having a boiling point higher than the alpha-olefin;

subjecting the product stream to an extractive distillation using methanol as a solvent, thereby yielding recovered methanol and at least one alpha-olefin selected from the group consisting of 1-pentene and an alpha-olefin having a boiling point lower than 1-pentene; and recycling the recovered methanol to the step of conducting an etherification.

2. The process according to claim 1, wherein the step of subjecting the product stream to an extractive distillation comprises the steps of:

feeding the product stream into an absorber, whereby oxygenates and dienes are separated, thereby yielding a remaining gaseous olefin stream and a liquid methanol stream, the remaining gaseous olefin stream comprising methanol and at least one alpha-olefin selected from the group consisting of 1-pentene and an alpha-olefin having a boiling point lower than 1-pentene, the liquid methanol stream comprising recovered methanol, oxygenates, dienes, and a small amount of olefins; and subjecting the remaining gaseous olefin stream to scrubbing with water, whereby methanol is removed, thereby yielding a scrubbed olefin stream and a methanol/water mixture, the scrubbed olefin stream comprising olefins and water.

3. The process according to claim 2, further comprising the step of subjecting the scrubbed olefin stream to a distillation drying step.

4. The process according to claim 2, further comprising the steps of:

cooling the scrubbed olefin stream, thereby forming a condensed scrubbed olefin stream;

decanting the condensed scrubbed olefin stream into a water fraction and a liquid olefins fraction containing dissolved water;

feeding the water fraction into a water scrubbing stage, whereby methanol is removed; and extracting dissolved water from the liquid olefin fraction in a heated drying column, whereby a dry olefin production stream is recovered.

5. The process according to claim 2, further comprising the step of:

passing the liquid methanol stream and the methanol/water mixture to a methanol stripper, whereby methanol is regenerated.

6. The process according to claim 5, further comprising the steps of:

obtaining a sump product from the methanol stripper, the sump product comprising substantially methanol-free water;

withdrawing a first methanol stream from a first side outlet of the methanol stripper, the first methanol stream containing a small amount of water and being substantially oxygenate-free and substantially diene-free, and using the first methanol stream in the absorber as a solvent; and withdrawing a second methanol stream from a second side outlet of the methanol stripper, the second methanol stream containing a small amount of water and being substantially oxygenate-free and substantially diene-free; and recycling the second methanol stream to the step of step of conducting an etherification.

7. The process according to claim 6, further comprising the steps of:

enriching oxygenates and dienes in a rising gas in a section of the methanol stripper above the second side outlet;

passing the rising gas by way of a chimney tray into a head portion of the methanol stripper;

scrubbing methanol out of the rising gas in the head portion of the methanol stripper by water scrubbing;

recovering an overhead gas and a scrubbing water, the overhead gas comprising oxygenate and dienes and being substantially methanol-free, the scrubbing water containing dissolved methanol; and forwarding the scrubbing water to a lower section of the methanol stripper.

8. The process according to claim 7, further comprising the steps of:

condensing the overhead gas, whereby a condensed overhead gas is obtained;

decanting the condensed overhead gas, whereby a water fraction and a fraction containing oxygenates and dienes are obtained;

using the water fraction for water scrubbing in the head portion of the methanol stripper;

feeding a first portion of the fraction containing oxygenates and dienes to below the chimney tray as a reflux liquid; and feeding a second portion of the fraction containing oxygenates and dienes as a by-product stream to a further use.

9. The process according to claim 8, further comprising the steps of:

using a first portion of the sump product comprising substantially methanol-free water for water scrubbing in the head portion of the methanol stripper; and using a second portion of the sump product comprising substantially methanol-free water for water scrubbing the remaining gaseous olefin stream.

10. The process according to claim 2, further comprising the steps of:

passing the liquid methanol stream to a methanol regenerating column; and passing the methanol/water mixture to a methanol/water separating column.

11. The process according to claim 9, further comprising the steps of:

passing the liquid methanol stream to a methanol regenerating column; and passing the methanol/water mixture to a methanol/water separating column.

12. The process according to claim 10, further comprising the steps of:

obtaining a water sump product and a methanol overhead product from the methanol/water separating column, wherein the water sump product is substantially methanol-free, substantially oxygenate-free, and substantially diene-free, and wherein the methanol overhead product is substantially methanol-free, substantially oxygenate-free, and substantially diene-free;

condensing the methanol overhead product, thereby yielding a condensed methanol overhead product;

using a first portion of the condensed methanol overhead product as a solvent in the methanol/water separating column; and feeding a second portion of the methanol overhead product into the methanol regeneration column.

13. The process according to claim 10, further comprising the steps of:

withdrawing a methanol sump product from a sump of the methanol regenerating column, the methanol sump product comprising methanol and being substantially oxygenate-free and substantially diene-free;

using a first portion of the methanol sump product as a solvent in the absorber; and recycling a second portion of the methanol sump product to the step of conducting an etherification.

14. The process according to claim 10, further comprising the steps of:

enriching oxygenates and dienes in a rising gas in the methanol regeneration column;

passing the rising gas by way of a chimney tray into a head portion of the methanol/water separating column;

scrubbing methanol out of the rising gas in the head portion of the methanol/water separating column by water scrubbing;

recovering an overhead gas and a scrubbing water, the overhead gas comprising oxygenate and dienes and being substantially methanol-free, the scrubbing water containing dissolved methanol; and passing the scrubbing water into the methanol/water separating column.

15. The process according to claim 14, further comprising the steps of:

condensing the overhead gas, whereby a condensed overhead gas is obtained;

decanting the condensed overhead gas, whereby a water fraction and a fraction containing oxygenates and dienes are obtained;

using the water fraction for water scrubbing in the overhead portion of the methanol regenerating column;

feeding a first portion of the fraction containing oxygenates and dienes to below the chimney tray as a reflux liquor; and passing a second portion of the fraction containing oxygenates and dienes as a by-product stream for a further use.

16. The process according to claim 10, further comprising the steps of:

obtaining a water sump product from the methanol/water separating column;

using a first portion of the water sump product for water scrubbing in the head portion of the methanol stripper; and using a second portion of the water sump product for water scrubbing of the remaining gaseous olefin stream.

* * * * *